(12) United States Patent
Schreiner

(10) Patent No.: US 7,291,734 B2
(45) Date of Patent: Nov. 6, 2007

(54) N-SULFONYLAMINOTHIAZOLE

(75) Inventor: Erwin P Schreiner, Vienna (AT)

(73) Assignee: Novartis AG, Basel (CH)

( * ) Notice: Subject to any disclaimer, the term of this patent is extended or adjusted under 35 U.S.C. 154(b) by 94 days.

(21) Appl. No.: 10/533,335

(22) PCT Filed: Nov. 13, 2003

(86) PCT No.: PCT/EP03/12707

§ 371 (c)(1),
(2), (4) Date: May 2, 2005

(87) PCT Pub. No.: WO2004/043968

PCT Pub. Date: May 27, 2004

(65) Prior Publication Data

US 2006/0247268 A1    Nov. 2, 2006

(30) Foreign Application Priority Data

Nov. 14, 2002 (GB) ................... 0226602.1
Nov. 14, 2002 (GB) ................... 0226616.1

(51) Int. Cl.
*C07D 471/02* (2006.01)
(52) U.S. Cl. ........................ 546/114; 546/82
(58) Field of Classification Search ................ 546/82, 546/114; 540/472, 581; 514/183, 214.03, 514/293, 301
See application file for complete search history.

(56) References Cited

FOREIGN PATENT DOCUMENTS

| DE | 24 29 195 | 6/1974 |
|---|---|---|
| GB | 1140387 | 1/1966 |
| JP | 2003183286 | 7/2003 |
| WO | 02/30358 | 4/2002 |

OTHER PUBLICATIONS

Yoshino T et al 'Preparation of ethylenediamine an d1,2-cycloalkanediamine derivatives as inhibitors of activated blood coagulation factor X' CA 135:303902 (2001).*
Barf, T et al 'Preparation of thiazolylbenzenesulfonamides and analogs as 11—hydroxysteroid dehydrogenase type 1 inhibitors for treatment of diabetes and related diseases' CA 136:5983 )2001).*
Moersdorf, P et al 'Preparation of hydrazinothiazolopyridines as antiinflammatories' CA 107:7185 (1987).*
Thomae, K '4,5,6,7-Tetrahydrothiazolo[5,4-c]pyridines' CA 68:49593 (1968).*
Nauubaumer et al, Steroid Sulfatase Inhibitors, Medicinal Research Reviews, vol. 24, No. 4, 529-576, 2004.*

* cited by examiner

*Primary Examiner*—Amelia Owens
(74) *Attorney, Agent, or Firm*—Gregory Houghton; Regina Bautista; Novartis

(57) ABSTRACT

N-(4,5,6,7-tetrahydro-thiazolo-[5,4-c]pyridin-2-yl)-($C_{6-18}$) arylsulfonamides, wherein the nitrogen atom of the pyridine is substituted, and wherein the pyridine ring is optionally bridged, useful as a pharmaceutical related to steroid sulfatase

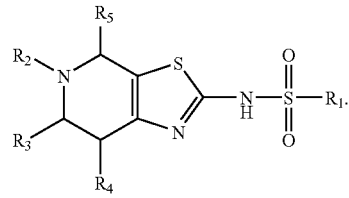

6 Claims, No Drawings

N-SULFONYLAMINOTHIAZOLE

The present invention relates to N-sulfonylaminothlazoles, e.g. useful in the treatment of disorders mediated by the action of steroid sulfatase.

In one aspect the present invention provides the use of N-(4,5,6,7-tetrahydro-thiazolo-[5,4-c]pyridin-2-yl)($C_{6-18}$)arylsulfonamides, wherein the nitrogen atom of the pyridine is substituted, e.g. and wherein the pyridine ring is optionally bridged, in the preparation of a medicament for the treatment of a disorder mediated by the action of steroid sulfatase, e.g. acne.

N-(4,5,6,7-tetrahydro-thiazolo-[5,4-c]pyridin-2-yl)-($C_{6-18}$)arylsulfonamides, wherein the nitrogen atom of the pyridine is substituted, e.g. and wherein the pyridine ring is optionally bridged, are herein designated as "Thiazolo-pyridine-arylsulfonamides of (according to) the present invention". The nitrogen atom of the pyridine is substituted, e.g. by ($C_{1-12}$)alkoxycarbonyl, ($C_{1-6}$)alkylcarbonyl, ($C_{3-6}$)cycloalkyl($C_{1-6}$)alkylcarbonyl, unsubstituted or substituted ($C_{6-18}$)aryl, one or morefold substituted, such as phenyl, e.g. ($C_{6-18}$)aryl substituted by aminocarbonyl, halogen or halo($C_{1-6}$)alkyl, such as aminocarbonyl or halo($C_{1-6}$)alkyl. Preferably the nitrogen atom of the pyridine is substituted by ($C_{1-12}$)alkoxycarbonyl, ($C_{3-6}$)cycloalkyl($C_{1-6}$)alkylcarbonyl, unsubstituted or substituted ($C_{6-18}$)aryl. The pyridine ring is unbridged or bridged, e.g. bridged by ($C_{1-4}$)alkylene, e.g. ($C_{1-2}$)alkylene, such as ethylene. Thiazolo-pyridine-arylsulfonamides of the present invention includes e.g. N-(4,5,6,7-tetrahydro-thiazolo[5,4-c]pyridin-2-yl)-benzenesulfonamides.

The ($C_{6-18}$)aryl group attached to the sulfonamide may be unsubstituted or substituted, e.g. substituted by groups as conventional in organic chemistry, such as halo($C_{1-4}$)alkyl or halogen.

In another aspect a thiazolo-pyridine-arylsulfonamides of the present invention for use provided by the present invention is a compound of formula

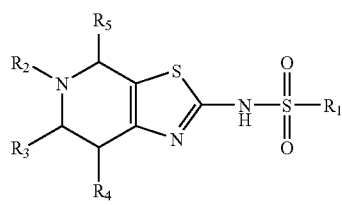

I wherein
$R_1$ is unsubstituted or substituted ($C_{6-18}$)aryl, e.g. substituted by aminocarbonyl, halogen or halo($C_{1-6}$)alkyl, preferably halogen or halo($C_{1-6}$)alkyl,
$R_2$ is ($C_{1-12}$)alkoxycarbonyl, ($C_{1-6}$)alkylcarbonyl, ($C_{3-6}$)cycloalkyl($C_{1-6}$)alkylcarbonyl or unsubstituted or substituted ($C_{6-18}$)aryl, e.g. substituted by aminocarbonyl, halogen or halo($C_{1-6}$)alkyl, and
EITHER
$R_3$, $R_4$ and $R_5$ are hydrogen
OR
$R_3$ and $R_5$ together are ($C_{1-4}$)alkylene and $R_4$ is hydrogen.

Thiazolo-pyridine-arylsulfonamides of the present invention, including compounds of formula I, for use in the preparation of a medicament for the treatment of a disorder mediated by the action of steroid sulfatase, are hereinafter designated as "compound(s) for use in (according to) the present invention".

Each single substituent defined in a thiazolo-pyridine-arylsulfonamides of the present invention may be per se a preferred substituent, independently of the other substituents defined.

In another aspect the present invention provides a compound of formula I which is a compound of formula

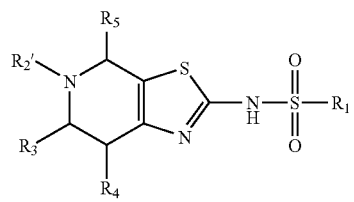

II wherein
$R_1$ is unsubstituted or substituted ($C_{6-18}$)aryl, e.g. substituted by aminocarbonyl, halogen or halo($C_{1-6}$)alkyl,
$R_2'$ is ($C_{1-12}$)alkoxycarbonyl, ($C_{1-6}$)alkylcarbonyl, ($C_{3-6}$)cycloalkyl($C_{1-6}$)alkylcarbonyl, or unsubstituted or substituted ($C_{6-18}$)aryl, e.g. substituted by aminocarbonyl, halogen or halo($C_{1-6}$)alkyl, and
$R_3$ and $R_6$ together are ($C_{1-4}$)alkylene and $R_4$ is hydrogen.

In a further aspect the present invention provides a compound of formula II, which is a compound of formula

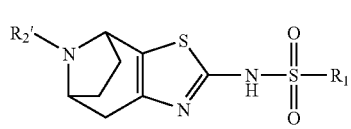

II$_A$ wherein
$R_1$ is phenyl substituted by halo($C_{1-4}$)alkyl or halogen, and
$R_2'$ is ($C_{1-6}$)alkoxycarbonyl, ($C_{3-6}$)cycloalkyl($C_{1-4}$)alkylcarbonyl or unsubstituted or substituted phenyl, e.g. phenyl one or morefold substituted by aminocarbonyl, halogen or halo($C_{1-6}$)alkyl.

In another aspect the present invention provides a compound of formula II or II$_A$, which is a compound of formula

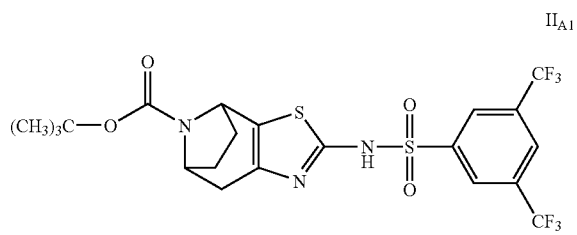

II$_{A1}$

In a further aspect the present invention provides a compound of formula I, which is a compound of formula

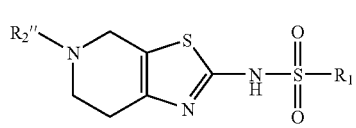

III wherein
$R_1$ is unsubstituted or substituted ($C_{6-18}$)aryl, e.g. substituted by aminocarbonyl, halogen or halo($C_{1-6}$)alkyl, and R$_2$″ is (C$_{1-12}$)alkoxycarbonyl, (C$_{3-6}$)cycloalkyl(C$_{1-6}$)alkylcarbonyl, unsubstituted (C$_{6-18}$)aryl, or (C$_{6-18}$)aryl substituted by aminocarbonyl, halogen or halo(C$_{1-6}$)alkyl.

In another aspect the present invention provides a compound of formula III, which is a compound of formula

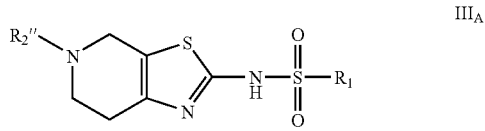

wherein

R$_1$ is phenyl substituted one or morefold by halo(C$_{1-4}$)alkyl or halogen, and R$_2$″ is (C$_{1-6}$)alkoxycarbonyl, (C$_{3-6}$)cycloalkyl(C$_{1-2}$)alkylcarbonyl, or phenyl substituted by aminocarbonyl or halo(C$_{1-4}$)alkyl.

In another aspect the present invention provides a compound of formula

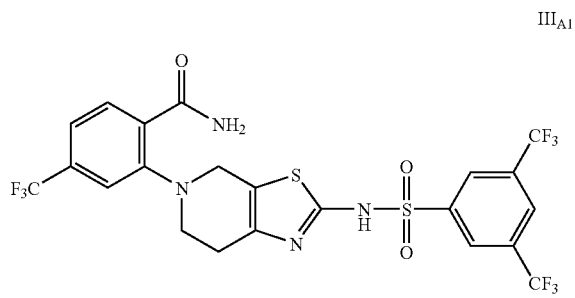

In another aspect the present invention provides a compound of formula II, which is N-(3-thia-5,11-diaza-tricyclo[6.2.1.0*2,6*]undeca-2(6),4-dien-4-yl)-benzenesulfonamide.

In another aspect the present invention provides a compound of formula III, which is selected from the group consisting of 2-[2-(3,5-Bis-trifluoromethyl-benzenesulfonylamino)-6,7-dihydro-4H-thiazolo[5,4-c]pyridin-5-yl]-4-trifluorolmethyl-benzamide, 2-[2-(2,3-Dichloro-benzenesulfonylamino)-6,7-dihydro-4H-thiazolo[5,4-c]pyridin-5-yl]-4-trifluoromethyl-benzamide, 2-[2-(3,5-Dichloro-benzenesulfonylamino)-6,7-dihydro-4H-thiazolo[5,4-c]pyridin-5-yl]-4-trifluoromethyl-benzamide, 2-(3,5-Bis-trifluoromethyl-benzenesulfonamino)-6,7-dihydro-4H-thiazolo[5,4-c]pyridine-5-carboxylic acid tert-butyl ester, 2-(2,3-Dichloro-benzenesulfonamino)-6,7-dihydro-4H-thiazolo[5,4-c]pyridine-5-carboxylic acid tert-butyl ester, 2-(3,5-Dichloro-benzenesulfonamino)-6,7-dihydro-4H-thiazolo[5,4-c]pyridine-5-carboxylic acid tert-butyl ester, and N-[5-(2-Cyclopentyl-acetyl)-4,5,6,7-tetrahydro-thiazolo[5,4-c]pyridin-2-yl]-3,5-bis-trifluoro-methyl-benzenesulfonamide.

If not otherwise defined herein (C$_{6-18}$)aryl includes unsubstituted and substituted (C$_{6-18}$) aryl, e.g. phenyl, such as (C$_{6-18}$)aryl, one or morefold substituted by groups as conventional in organic chemistry, e.g. including aminocarbonyl, halogen or halo(C$_{1-6}$) alkyl.

halo(C$_{1-6}$)alkyl includes halo(C$_{1-4}$)alkyl, such as CF$_3$, halogen includes fluoro, chloro, bromo and iodo, such as chloro, (C$_{1-12}$)alkoxy includes (C$_{1-6}$)alkoxy, such as (C$_{1-4}$)alkoxy, e.g. tert.butoxy, (C$_{3-6}$)cycloalkyl includes (C$_{5-6}$)cycloalkyl, such as pentyl, (C$_{1-6}$)alkylcarbonyl includes (C$_{1-4}$)alkylcarbonyl, such as methylcarbonyl, Compounds provided by the present invention, such as compounds of formula II, II$_A$, II$_{A1}$, III, III$_A$ and III$_{A1}$, are hereinafter designated as "compound(s) of (according to) the present Invention". Each single substituent defined above in a compound of the present invention may be per se a preferred substituent, independently of the other substituents defined. A compound of formula II includes compounds of formulae II$_A$ and II$_{A1}$. A compound of formula III includes compounds of formulae III$_A$ and III$_{A1}$.

A compound of the present invention includes a compound in any form, e.g. in free form, in the form of a salt, in the form of a solvate and in the form of a salt and a solvate.

In another aspect the present invention provides a compound of the present invention in the form of a salt.

A compound for use in the present invention may be used in any form, e.g. in free form, in the form of a salt, in the form of a solvate and in the form of a salt and a solvate.

A salt of a compound of the present invention or of a compound for use in the present invention includes a pharmaceutically acceptable salt, e.g. including metal salts, and acid addition salts. Metal salts include for example alkali or earth alkali salts; e.g. sodium, acid addition salts include salts of a compound of the present invention or a compound for use in the present invention with an acid, e.g. HCl.

A compound of the present invention or a compound for use in the present invention in free form may be converted into a corresponding compound in the form of a salt; and vice versa. A compound of the present invention or a compound for use in the present invention in free form or in the form of a salt and in the form of a solvate may be converted into a corresponding compound in free form or in the form of a salt in unsolvated form; and vice versa.

A compound of the present invention or a compound for use in the present invention may exist in the form of isomers and mixtures thereof. Isomeric, e.g. including enantiomeric or diasteromeric mixtures, may be separated as appropriate, e.g. according to a method as conventional, to obtain pure isomers. The present invention includes a compound of the present invention or a compound for use in the present invention in any isomeric form and in any isomeric mixture.

In a further aspect the present invention provides a process for the production of a compound of the present invention, e.g. or a a process for the production of a compound for use in the present invention, comprising reacting an 4,5,6,7-tetrahydro-thiazolo[5,4-c]pyridin-2-yl-amine, e.g. of formula

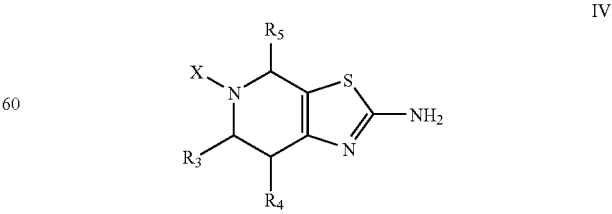

wherein X has the meaning of R$_2$, R$_2$′ or R$_2$″ as defined above and R$_3$, R$_4$ and R$_5$ are as defined above, with an appropriate sulfonylhalogenide, e.g. chloride, such as a compound of formula $R_1$—$SO_2Cl$, wherein $R_1$ is as defined above, to obtain a compound of the present invention, e.g. or a compound for use in the present invention.

In a preferred embodiment of the present invention a compound of the present invention or a compound for use in the present invention may be prepared by the following steps a. reacting of a compound of formula IV, wherein X is tert.butoxycarbonyl and $R_3$, $R_4$ and $R_5$ are as defined above, with a compound of formula $R_1$—$SO_2Cl$, wherein $R_1$ is as defined above, to obtain a compound of formula I or of formula II or of formula III, wherein $R_1$, $R_3$, $R_4$ and $R_5$ are as defined above and X is tert.butoxycarbonyl, and b. splitting off the tert.butoxycarbonyl group, e.g. by treatment with etheric HCl, to obtain a compound of formula

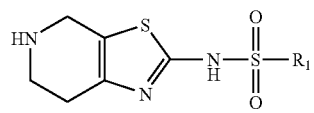

V wherein $R_1$ is as defined above, e.g. in the form of a salt, such as a hydrochloride, c. either reacting a compound of formula V c1. with a (substituted) phenylfluoride to obtain a compound of formula I or of formula II or fo formula III, wherein $R_1$ is as defined above and $R_2$, $R_2'$ or $R_2''$ is a (substituted) phenyl, or c2. with a ($C_{3-6}$)cycloalkyl($C_{1-6}$)alkylcarbonylhalogenide, e.g. chloride, to obtain a compound of formula I or of formula II or of formula II, wherein $R_1$ is as defined above and $R_2$, $R_2'$ or $R_2''$ is ($C_{3-6}$)cycloalkyl($C_{1-6}$)alkylcarbonyl, and d. isolating a compound of formula I or formula III obtained from the reaction mixture.

Compounds of formulae IV and V are useful as an intermediate for the preparation of a compound of formula I or of formula III. A compound of formula IV also forms part of the present invention.

In another aspect the present invention provides a compound of formula

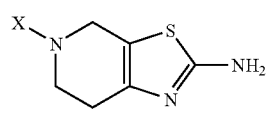

IV wherein X has the meaning of $R_2''$ as defined above, e.g. in the form of a salt, such as a hydrochloride, e.g. as an Intermediate in the preparation of a compound of formula III.

In another aspect the present invention provides a process for the production of a compound of the present invention, e.g. or a compound for use in the present invention, comprising reacting an 4,5,6,7-tetrahydro-thiazolo[5,4-c]pyridin-2-yl-amine, e.g. of formula

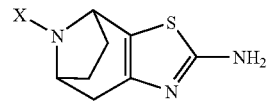

VI wherein X has the meaning of $R_2'$ as defined above, with an sulfonylhalogenide, e.g. chloride, such as a compound of formula $R_1$—$SO_2Cl$, wherein $R_1$ is as defined above, to obtain a compound of the present invention, e.g. or a compound for use in the present invention, e.g. a compound of formula I or of formula II.

Compounds of formula VI and VII are useful as an intermediate for the preparation of a compound of formula I or of formula II or formula III, and also form part of the present invention.

In another aspect the present invention provides a compound of formula

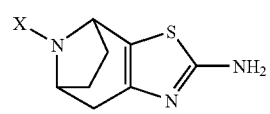

VI wherein X has the meaning of $R_2'$ as defined above, e.g. in the form of a salt, such as a hydrochloride, e.g. as an Intermediate in the preparation of a compound of formula I or formula II.

In another aspect the present invention provides a compound of formula

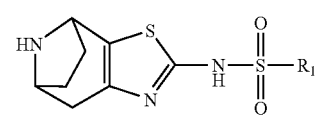

VII wherein $R_1$ is as defined above, e.g. in the form of a salt, such as a hydrochloride, e.g. as an intermediate in the preparation of a compound of formula I or of formula II.

The above reactions are acylation reactions and may be carried out as appropriate, e.g. in appropriate solvent and at appropriate temperatures, e.g. according, e.g. analogously, to a method as conventional or as described herein.

A compound of formula I or of formula II or formula III may be converted in its sodium salt e.g. by treatment of a compound of formula I or of formula II or formula III in free base form with NaOH, e.g. in EtOH, to obtain a compound of formula I or of formula II or of formula III, wherein the nitrogen of the sulfonamide group is in the form of an anion with Na as a cation.

A compound of formula IV may be obtained as appropriate, e.g. according, e.g. analogously, to a method as conventional, e.g. by reacting an N-substituted piperidone with cyanamide in the presence of sulfur in a polar solvent, e.g. pyridine.

Any compound described herein, e.g. including compounds of the present invention, or compounds for use in the present invention, and intermediates in their preparation, e.g. including compounds of formulae IV, V, VI or VII, may be prepared as appropriate, e.g. according, e.g. analogously, to a method as conventional, e.g. or as specified herein.

In an intermediate of the present invention, functional groups, if present, optionally may be in protected form or in the form of a salt, if a salt-forming group is present. Protecting groups, optionally present, may be removed at an appropriate stage, e.g. according, e.g. analogously, to a method as conventional.

Steroidal hormones in particular tissues are associated with several diseases, such as tumors of breast, endometrium and prostate and disorders of the pilosebaceous unit, e.g. acne, androgenetic alopecia, and hirsutism. Important precursors for the local production of these steroid hormones are steroid 3-O-sulfates which are desulfated by the enzyme steroid sulfatase in the target tissues. Inhibition of this enzyme results in reduced local levels of the corresponding active steroidal hormones, which is expected to be of therapeutic relevance. Furthermore, steroid sulfatase inhibitors may be useful as immunosuppressive agents, and have been shown to enhance memory when delivered to the brain.

Acne is a polyetiological disease caused by the interplay of numerous factors, such as inheritance, sebum, hormones, and bacteria. The most important causative factor in acne is sebum production; in almost all acne patients sebaceous glands are larger and more sebum is produced than in persons with healthy skin. The development of the sebaceous gland and the extent of sebum production is controlled hormonally by androgens; therefore, androgens play a crucial role in the pathogenesis of acne. In man, there are two major sources supplying androgens to target tissues: (i) the gonades which secrete testosterone, (ii) the adrenals producing dehydroepiandrosterone (DHEA) which is secreted as the sulfate conjugate (DHEAS). Testosterone and DHEAS are both converted to the most active androgen, dihydrotestosterone (DHT), in the target tissue, e.g. in the skin. There is evidence that these pathways of local synthesis of DHT in the skin are more important than direct supply with active androgens from the circulation. Therefore, reduction of endogeneous levels of androgens in the target tissue by specific inhibitors should be of therapeutic benefit in acne and seborrhoea. Furthermore, it opens the perspective to treat these disorders through modulation of local androgen levels by topical treatment, rather than influencing circulating hormone levels by systemic therapies.

Androgenetic male alopecia is very common in the white races, accounting for about 95% of all types of alopecia. Male-pattern baldness is caused by an increased number of hair follicles in the scalp entering the telogen phase and by the telogen phase lasting longer. It is a genetically determined hair loss effected through androgens. Elevated serum DHEA but normal testosterone levels have been reported in balding men compared with non-balding controls, implying that target tissue androgen production is important in androgenetic alopecia.

Hirsutism is the pathological thickening and strengthening of the hair which is characterized by a masculine pattern of hair growth in children and women. Hirsutism is androgen induced, either by increased formation of androgens or by increased sensitivity of the hair follicle to androgens. Therefore, a therapy resulting in reduction of endogeneous levels of androgens and/or estrogens in the target tissue (skin) should be effective in acne, androgenetic alopecia and hirsutism.

As described above, DHT, the most active androgen, is synthesized in the skin from the abundant systemic precursor DHEAS and the first step in the metabolic pathway from DHEAS to DHT is desulfatation of DHEAS by the enzyme steroid sulfatase to produce DHEA. The presence of the enzyme in keratinocytes and in skin-derived fibroblasts has been described. The potential use of steroid sulfatase inhibitors for the reduction of endogenous levels of steroid hormones in the skin was confirmed using known steroid sulfatase inhibitors, such as estrone 3-O-sulfamate and 4-methylumbelliferyl-7-O-sulfamate. We have found that inhibitors of placental steroid sulfatase also inhibit steroid sulfatase prepared from either a human keratinocyte (HaCaT) or a human skin-derived fibroblast cell line (1BR3GN). Such inhibitors were also shown to block steroid sulfatase in intact monolayers of the HaCaT keratinocytes.

Therefore, Inhibitors of steroid sulfatase may be used to reduce androgen and estrogen levels in the skin. They can be used as inhibitors of the enzyme steroid sulfatase for the local treatment of androgen-dependent disorders of the pilosebaceous unit (such as acne, seborrhoea, androgenetic alopecia, hirsutism) and for the local treatment of squamous cell carcinoma.

Furthermore non-steroidal steroid sulfatase inhibitors are expected to be useful for the treatment of disorders mediated by the action of steroid hormones in which the steroidal products of the sulfatase cleavage play a role. Indications for these new kind of inhibitors include androgen-dependent disorders of the pilosebaceous unit (such as acne, seborrhea, androgenetic alopecia, hirsutism); estrogen- or androgen-dependent tumors, such as squamous cell carcinoma and neoplasms, e.g. of the breast, endometrium, and prostate; inflammatory and autoimmune diseases, such as rheumatoid arthritis, type I and II diabetes, systemic lupus erythematosus, multiple sclerosis, myasthenia gravis, thyroiditis, vasculitis, ulcerative colitis, and Crohn's disease, psoriasis, contact dermatitis, graft versus host disease, eczema, asthma and organ rejection following transplantation. Steroid sulfatase inhibitors are also useful for the treatment of cancer, especially for the treatment of estrogen- and androgen-dependent cancers, such as cancer of the breast and endometrium and squamous cell carcinoma, and cancer of the prostata. Steroid sulfatase inhibitors are also useful for the enhancement of cognitive function, especially in the treatment of senile dementia, including Alzheimer's disease, by increasing the DHEAS levels in the central nervous system.

Activities of compounds in inhibiting the activity of steroid sulfatase may be shown in the following test systems:

Purification of Human Steroid Sulfatase

Human placenta is obtained freshly after delivery and stripped of membranes and connective tissues. For storage, the material is frozen at −70° C. After thawing, all further steps are carried out at 4° C., while pH values are adjusted at 20° C. 400 g of the tissue is homogenized in 1.2 l of buffer A (50 mM Tris-HCl, pH 7.4, 0.25 M sucrose). The homogenate obtained is centrifuged at 10,000×g for 45 minutes. The supernatant is set aside and the pellet obtained is re-homogenized in 500 ml of buffer A. After centrifugation, the two supernatants obtained are combined and subjected to ultracentrifugation (100,000×g, 1 hour). The pellet obtained is resuspended in buffer A and centrifugation is repeated. The pellet obtained is suspended in 50 ml of 50 mM Tris-HCl, pH 7.4 and stored at −20° C. until further work-up.

After thawing, microsomes are collected by ultracentrifugation (as descrobed above) and are suspended in 50 ml of buffer B (10 mM Tris-HCl, pH 7.0, 1 mM EDTA, 2 mM 2-mercaptoethanol, 1% Triton X-100, 0.1% aprotinin). After 1 hour on ice with gentle agitation, the suspension is centrifuged (100,000×g, 1 hour). The supernatant containing the enzyme activity is collected and the pH is adjusted to 8.0 with 1 M Tris. The solution obtained is applied to a hydroxy apatite column (2.6×20 cm) and equilibrated with buffer B, pH 8.0. The column is washed with buffer B at a flow rate of 2 ml/min. The activity is recovered in the flow-through. The pool is adjusted to pH 7.4 and subjected to chromatography on a concanavalin A sepharose column (1.6×10 cm) equilibrated in buffer C (20 mM Tris-HCl, pH 7.4, 0.1% Triton X-100, 0.5 M NaCl). The column is washed with buffer C, and the bound protein is eluted with 10% methyl mannoside in buffer C. Active fractions are pooled and dialysed against buffer D (20 mM Tris-HCl, pH 8.0, 1 mM EDTA, 0.1% Triton X-100, 10% glycerol (v/v)).

The retentate obtained is applied to a blue sepharose column (0.8×10 cm) equilibrated with buffer D; which column is washed and elution is carried out with a linear gradient of buffer D to 2 M NaCl in buffer D. Active fractions are pooled, concentrated as required (Centricon 10), dialysed against buffer D and stored in aliquots at −20° C.

Assay of Human Steroid Sulfatase

It is known that purified human steroid sulfatase not only is capable to cleave steroid sulfates, but also readily cleaves aryl sulfates such as 4-methylumbelliferyl sulfate which is used in the present test system as an activity indicator. Assay mixtures are prepared by consecutively dispensing the following solutions into the wells of white microtiter plates:

1) 50 µl substrate solution (1.5 mM 4-methylumbelliferyl sulfate in 0.1 M Tris-HCl, pH 7.5)
2) 50 µl test compound dilution in 0.1 M Tris-HCl, pH 7.5, 0.1% Triton X-100 (stock solutions of the test compounds are prepared in DMSO; final concentrations of the solvent in the assay mixture not exceeding 1%)
3) 50 µl enzyme dilution (approximately 12 enzyme units/ml)

We define one enzyme unit as the amount of steroid sulfatase that hydrolyses 1 nmol of 4-methylumbelliferyl sulfate per hour at an initial substrate concentration of 500 µM in 0.1 M Tris-HCl, pH 7.5, 0.1% Triton X-100, at 37° C.

Plates are incubated at 37° C. for 1 hour. Then the reaction is stopped by addition of 100 µl 0.2 M NaOH. Fluorescence intensity is determined in a Titertek Fluoroskan II instrument with $\lambda_{ex}=355$ nm and $\lambda_{em}=460$ nm.

Calculation of Relative $IC_{50}$ Values

From the fluorescence intensity data (I) obtained at different concentrations (c) of the test compound in the human steroid sulfatase assay as described above, the concentration inhibiting the enzymatic activity by 50% ($IC_{50}$) is calculated using the equation:

$$I = \frac{I_{100}}{1 + (c/IC_{50})^s}$$

wherein $I_{100}$ is the intensity observed in the absence of inhibitor and s is a slope factor. Estrone sulfamate is used as a reference compound and its $IC_{50}$ value is determined in parallel to all other test compounds. Relative $IC_{50}$ values are defined as follows:

$$rel\ IC_{50} = \frac{IC_{50}\ of\ test\ compound}{IC_{50}\ of\ estrone\ sulfamate}$$

According to our testing and calculation estrone sulfamate shows an $IC_{50}$ value of approximately 60 nM.

The compounds for use in the present invention including the compounds of the present invention show activity in that described assay.

CHO/STS Assay

CHO cells stably transfected with human steroid sulfatase (CHO/STS) are seeded into microtiter plates. After reaching approximately 90% confluency, they are incubated overnight with graded concentrations of test substances (e.g. compounds of the present invention or compounds for use in the present invention). They are then fixed with 4% paraformaldehyde for 10 minutes at room temperature and washed 4 times with PBS, before incubation with 100 µl/well 0.5 mM 4-methylumbelliferyl sulfate (MUS), dissolved in 0.1M Tris-HCl, pH 7.5. The enzyme reaction is carried out at 37° C. for 30 minutes. Then 50 µl/well stop solution (1 M Tris-HCl, pH 10.4) are added. The enzyme reaction solutions are transferred to white plates (Microfluor, Dynex, Chantilly, Va.) and read in a Fluoroskan II fluorescence microtiter plate reader. Reagent blanks are subtracted from all values. For drug testing, the fluorescence units (FU) are divided by the optical density readings after staining cellular protein with sulforhodamine B ($OD_{550}$), in order to correct for variations in cell number. $IC_{50}$ values are determined by linear interpolation between two bracketing points. In each assay with Inhibitors, estrone 3-O-sulfamate is run as a reference compound, and the $IC_{50}$ values are normalized to estrone 3-O-sulfamate (relative $IC_{50}=IC_{50}$ compound/$IC_{50}$ estrone 3-O-sulfamate).

The compounds for use in the present Invention including the compounds of the present Invention show activity in that described assay.

Assay Using Human Skin Homogenate

Frozen specimens of human cadaver skin (about 100 mg per sample) are minced into small pieces (about 1×1 mm) using sharp scissors. The pieces obtained are suspended in ten volumes (w/w) of buffer (20 mM Tris-HCl, pH 7.5), containing 0.1% Triton X-100. Test compounds (e.g. compounds of the present invention or compounds for use in the present invention) are added at graded concentrations from stock solutions in ethanol or DMSO. Second, DHEAS as the substrate is added (1 µC/ml [$^3$H]DHEAS, specific activity: about 60 Cl/mmol, and 20 µM unlabeled DHEAS). Samples are incubated for 18 hrs at 37° C. At the end of the incubation period, 50 µl of 1 M Tris, pH 10.4 and 3 ml of toluene are added. A 1-ml aliquot of the organic phase is removed and subjected to liquid scintillation counting. The determined dpm-values in the aliquots are converted to nmol of DHEA cleaved per g of skin per hour.

The compounds for use in the present invention including the compounds of the present invention show activity in that described assay.

The compounds for use in the present invention including the compounds of the present invention show activity in test systems as defined above. A compound for use in the present invention including a compound of the present invention in salt and/or solvate form exhibits the same order of activity as a compound of the present invention or a compound for use in the present invention in free and/or non-solvated form.

The compounds for use in the present invention including the compounds of the present invention are therefore indicated for use as steroid sulfatase inhibitors in the treatment of disorders mediated by the action of steroid sulfatase, e.g. including androgen-dependent disorders of the pilosebaceous unit, such as acne, seborrhea, androgenetic alopecia, hirsutism;

cancers, such as estrogen and androgen-dependent cancers; cognitive dysfunctions, such as senile dementia including Alzheimer's disease.

The compounds for use in the present invention including the compounds of the present invention are preferably used in the treatment of acne, seborrhea, androgenetic alopecia, hirsutism; estrogen, e.g. and androgen-dependent cancers, more preferably in the treatment of acne. Treatment includes therapeutical treatment and prophylaxis.

The compound of example 1 is a preferred compound of the present invention. It has, for example been determined that a compound of example 1 shows an $IC_{50}$ of 160 nm in the assay using human skin homonegnate as described herein.

In another aspect the present invention provides a compound of formula II or of formula III for use as a pharmaceutical, e.g. in the treatment of disorders mediated by the action of steroid sulfatase.

In another aspect the present invention provides a method of treating disorders mediated by the action of steroid sulfatase, e.g. in the treatment of acne, seborrhea, androgenetic alopecia, hirsutism; estrogen, e.g. and androgen-dependent cancers, comprising administering a therapeutically effective amount of a thiazolo-pyridine-arylsulfonamides of the present invention e.g. including a compound of formula I or of formula II or of formula III, to a subject in need of such treatment.

For such use the dosage to be used will vary, of course, depending e.g. on the particular compound employed, the mode of administration and the treatment desired. However, in general, satisfactory results may be obtained if the compounds are administered at a daily dose of from about 0.1 mg/kg to about 100 mg/kg animal body weight (e.g. from about 0.0625 mg/kg to about 62.5 mg/kg), e.g. conveniently administered in divided doses two to four times daily. For most large mammals the total daily dosage is from about 5 mg to about 5000 mg, conveniently administered, for example, in divided doses up to four times a day or in retarded form. Unit dosage forms comprise, e.g. from about 1.25 mg to about 2000 mg of a compound of a present invention in admixture with at least one pharmaceutically acceptable excipient, e.g. carrier, diluent.

The compounds for use in the present invention including the compounds of the present invention may be administered in the form of a pharmaceutically acceptable salt, e.g. an acid addition salt or metal salt; or in free form; optionally in the form of a solvate.

The compounds for use in the present invention including the compounds of the present invention may be administered in similar manner to known standards for use in such indications. The compounds of the present invention or the compounds for use in the present invention may be admixed with conventional, e.g. pharmaceutically acceptable, exipients, such as carriers and diluents and optionally further exipients. The compounds for use in the present invention including the compounds of the present invention may be administered, e.g. in the form of pharmaceutical compositions, orally, e.g. in the form of tablets, capsules;
parenterally, intravenously, e.g. in the form of liquids, such as solutions, suspensions;
topically, e.g. in the form of ointments, creams.

The concentrations of the active substance in a pharmaceutical composition will of course vary, e.g. depending on the compound used, the treatment desired and the nature of the composition used. In general, satisfactory results may be obtained at concentrations of from about 0.05 to about 5% such as from about 0.1 to about 1% w/w in topical compositions, and by about 1% w/w to about 90% w/w in oral, parenteral or intravenous compositions.

In another aspect the present invention provides a pharmaceutical composition comprising a pharmaceutically effective amount of at least one compound of the present invention in association with at least one pharmaceutically acceptable excipient.

A pharmaceutical composition of the present invention may comprise as an active ingredient one or more compounds of the present invention, e.g. at least one.

Beside at least one compound of the present invention a pharmaceutical composition of the present invention may comprise one or more other pharmaceutically active agents. Such further pharmaceutically active agents include e.g. retinoids, e.g. retinoic acid, such as isotretinoin; tretinoin (Roche); adapalene (6-[3-(1-adamantyl)-4-methoxyphenyl]-2-naphthoic acid); oral contraceptives, e.g. 19-nor-17a-pregna-1,3,5(10)-trien-20-in-3,17-diol, 6-Chlor-17-hydroxy-1a,2a-methylen-4,6-pregnadien-3,20-dion, such as Diane® (Schering), antibacterials, such as erythromycins, including erythromycin A, azithromycin, clarithromycin, roxythromycin; tetracyclines, lincosamid-antbiotics, such as clindamycin (methyl 7-chlor-6,7,8-tridesoxy-6-trans-1-methyl-4-propyl-L-2-pyrrolidin-carboxamido)-1-thio-L-threo-a-D-galacto-octopyranosid azelaic acid (nonanedionic acid), nadifloxacin; dapsone, benzoyl peroxide; keratolytics, such as salicylic add; anti-inflammatory agents, such as corticosteroids, pimecrolimus; steroid 5α-reductase inhibitors.

For the treatment of breast and endometrial cancer further pharmaceutically active agents include aromatase inhibitors, such as anastrozole, letrozole, exemestane.

Combinations Include fixed combinations, in which two or more pharmaceutically active agents are in the same pharmaceutical composition,
kits, in which two or more pharmaceutically active agents in separate compositions are sold in the same package, e.g. with instruction for co-administration; and
free combinations in which the pharmaceutically active agents are packaged separately, but instruction for simultaneous or sequential administration are given.

In another aspect the present invention provides a compound of the present invention or a compound for use in the present invention in combination with at least one other pharmaceutically effective agent for use as a pharmaceutical, such as a pharmaceutical composition comprising a combination of at least one compound of the present invention or one compound for use in the present invention with at least one other pharmaceutically effective agent in association with at least one pharmaceutical acceptable excipient In another aspect the present invention provides a compound of formula

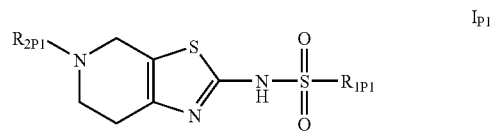

I$_{P1}$ wherein

R$_{1P1}$, is (C$_{6-18}$)aryl, and

R$_{2P1}$ is (C$_{1-12}$)alkoxycarbonyl, or unsubstituted or substituted phenyl, e.g. phenyl substituted by one or more groups selected from the group consisting of aminocarbonyl,
halogen,
$(C_{1-6})$haloalkyl.

In another aspect the present invention provides a compound of formula

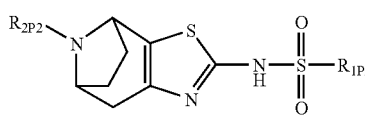

wherein $R_1$ is $(C_{6-18})$aryl, and $R_2$ is $(C_{1-12})$alkoxycarbonyl, $(C_{1-4})$alkylcarbonyl, or unsubstituted or substituted phenyl, e.g. phenyl substituted by one or more
aminocarbonyl,
halogen,
$(C_{1-6})$haloalkyl.

In the following examples which illustrate the invention references to temperature are in degree Centigrade and are uncorrected.

The following abbreviations are used:
BOC tert.-butyloxycarbonyl
c-Hex cyclohexanol
DMSO dimethylsulfoxide
DMAP N,N-dimethylaminopyridine
DIEA diisopropylethylamine
EtAc ethyl acetate
EtOH ethanol
m.p. melting point
RT room temperature

EXAMPLE 1

2-[2-(3,5-Bis-trifluoromethyl-benzenesulfonylamino)-6,7-dihydro-4H-thiazolo-[5,4-c]pyridin-yl] 4-trifluoromethyl-benzamide A. Free Base 3.3 g of 2-(3,5-bis-trifluoromethyl-benzenesulfonylamino)-4,5,6,7-tetrahydro-thiazolo[5,4-c]pyridin-5-ium hydrochloride, 1.545 g of 2-fluoro-4-trifluoromethyl-benzamide and 3.3 g of $K_2CO_3$ are heated in DMSO at 150° for 5 hours. From the mixture obtained solvent is evaporated, the evaporation residue obtained is dissolved in EtAc/MeOH (9/1) and the mixture obtained is extracted with 50 ml of 1 M HCl and brine. Two phases are obtained and are separated and the organic layer obtained is concentrated and subjected to chromatography. 2-[2-(3,5-Bis-trifluoromethyl-benzenesulfonylamino)-6,7-dihydro-4H-thiazolo-[5,4-c]pyridin-5-yl]-4-trifluoromethyl-benzamide is obtained and is re-crystallized from EtAc.

m.p.: 225-228°; $^1$H-NMR/CD$_3$OD: 8.35 (s, 2H), 8.03 (s, 1H), 7.92 (d, J=8.0 Hz, 1 H), 7.40 (dd, J=8.0, 1.1 Hz, 1H), 7.35 (s, 1H), 4.06 (t, J=1.8 Hz, 2H), 3.44 (t, J=5.6 Hz, 2 H), 2.69 (m, 2H); $^{13}$C-NMR/CD$_3$OD: 168.83, 149.35, 144.47, 133.37, 133.11, 131.99, 131.72, 131.08, 130.83, 126.07, 124.89, 123.27, 119.90, 116.27, 116.24, 113.20, 49.44, 47.90, 22.76.

B. Sodium Salt 1.9 ml of an aqueous 0.1 M NaOH solution are added to a solution of 118 mg of 2-[2-(3,5-bis-trifluoromethyl-benzenesulfonylamino)-6,7-dihydro-4H-thiazolo-[5,4-c]pyridin-5-yl]-4-trifluoromethyl-benzamide in 10 ml of EtOH, and the mixture obtained is stirred at RT for 5 minutes. From the mixture obtained solvent is evaporated and the evaporation residue obtained is subjected to lyophilisation. [2-(3, 5-Bis-trifluoromethyl-benzenesulfonylamino)-6,7-dihydro-4H-thiazolo-[5,4-c]pyridin-5-yl]-4-trifluoromethyl-benzamide sodium salt is obtained.

Analogously to the method as described in example 1A, but using appropriate starting materials, compounds of formula

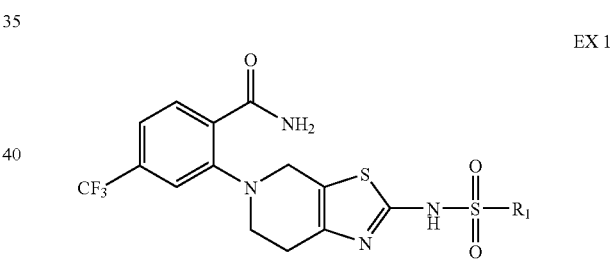

wherein $R_1$ is as defined in TABLE 1, are obtained. $^1$H-NMR and $^{13}$C-NMR data are also indicated in TABLE 1.

TABLE 1

| EX. | $R_1$ | $^1$H-NMR in CDCl$_3$ or $^{13}$C-NMR |
|---|---|---|
| 1 | 3,5-bis(CF$_3$)phenyl | $^1$H-NMR/CDCl$_3$/CD$_3$OD: 8.45(s, 2H), 8.03(d, J=7.9 Hz, 1H), 7.94(s, 1H), 7.43(d, J=7.9, Hz, 1H), 7.42(s, 1H), 4.08(s, 2H), 3.44(t, J=5.7 Hz, 2H), 2.74(t, J=5.6 Hz, 2 H); $^{13}$C-NMR/CDCl$_3$/CD$_3$OD: 168.92, 168.35, 151.59, 146.76, 141.82, 134.49, 134.17, 132.56, 132.30, 132.22, 131.89, 131.55, 130.91, 127.55, 125.16, 124.60, 122.45, 121.95, 120.89, 117.75, 115.34, 51.78, 50.04, 26.71. |
| 2 | 2,6-dichlorophenyl | $^{13}$C-NMR: 168.92, 168.81, 150.39, 14257, 135.40, 134.21, 133.35, 132.01, 131.02, 129.24, 128.11, 120.15, 117.01, 113.68, 50.35, 48.84, 24.27. |

TABLE 1-continued

| EX. | R₁ | ¹H-NMR in CDCl₃ or ¹³C-NMR |
|---|---|---|
| 3 | 3,5-dichlorophenyl | ¹³C-NMR: 168.64, 154.30, 145.48, 135.73, 132.77, 132.43, 127.25, 125.62, 115.24, 81.45, 52.24, 49.95, 34.89, 33.98, 31.49, 28.71 |

EXAMPLE 4

2-(3,5-Bis-trifluoromethyl-benzenesulfonylamino)-6,7-dihydro-4H-thiazolo-[5,4-c]pyridine-5-carboxylic acid tert-butyl ester A mixture of 8.5 g of 2-amino-6,7-dihydro-4H-thiazolo[5,4-c]pyridine-5-arboxylic acid tert.-butyl ester, 15.6 g of 3,5-bis-trifluoromethyl-benzenesulfonyl chloride, and 8.1 g of DMAP in 100 ml of pyridine is stirred at 80° for 4 hours. From the mixture obtained solvent is evaporated, the evaporation residue obtained is treated with EtAc and the mixture obtained is extracted with aqueous NaHSO₄ solution and brine. The organic layer obtained is dried, from the solution obtained solvent is evaporated and the residue obtained is treated with a mixture of EtAc and c-Hex (+5% MeOH). 2-(3,5-bis-trifluoromethylbenzenesulfonyl-amino)-6,7-dihydro-4H-thiazolo[5,4-c]pyridine-5-carboxylic acid tertbutyl ester precipitates, is filtrated off and dried.

Analogously to the method as described in example 4, but using appropriate starting materials, compounds of formula

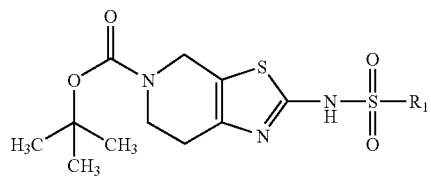

EX 2 wherein R₁ is as defined in TABLE 2, are obtained: ¹H-NMR and ¹³C-NMR data are also indicated in TABLE 2.

TABLE 2

| EX. | R₁ | ¹³H-NMR in CDCl₃ or ¹³C-NMR |
|---|---|---|
| 4 | 3,5-bis(trifluoromethyl)phenyl | ¹H-NMR/CDCl₃: 11.40(bs, 1H), 8.31(s, 2H), 8.03(s, 1H), 4.39 (s, 2H), 3.72(t, J=5.5 Hz, 2H), 2.78(t, J=5.6 Hz, 2H), 1.48(s, 9H); ¹³C-NMR/CDCl₃: 169.79, 154.58, 144.23, 133.52, 133.18, 132.84, 132.50, 131.61, 127.26, 126.97, 126.34, 124.25, 121.54, 118.82, 81.48, 28.68, 24.04. |
| 5 | 2,3-dichlorophenyl | ¹³C-NMR: 169.71, 140.50, 136.08, 134.48, 131.98, 130.93, 129.81, 127.26, 81.29, 28.72, 24.25. |
| 6 | 3,5-dichlorophenyl | ¹³C-NMR: 169.84, 154.65, 136.16, 132.79, 131.63, 125.46, 81.45, 28.73, 24.16. |

EXAMPLE 7

A compound of formula

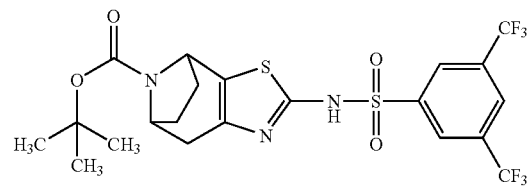

is obtained analogously to the method as described in example 4, but using appropriate starting materials $^{13}$C-NMR: 133.04, 132.70, 132.36, 129.39, 127.24, 126.09, 124.33, 121.61, 81.24, 52.70, 51.50, 32.30, 28.64.

EXAMPLE 8

N-[5-(2-Cyclopentyl-acetyl)-4,5,6,7-tetrahydro-thiazolo[5,4-c]pyridin-2-yl]-3,5-bis-trifluoromethyl-benzenesulfonamide DIEA and cyclopentyl-acetyl chloride are added at 0° to a mixture of 75 mg of 2-(3,5-bis-trifluoromethyl-benzenesulfonylamino)-4,5,6,7-tetrahydro-thiazolo[5,4-c]pyridin-5-ium hydrochloride salt in $CH_2Cl_2$. The mixture obtained is stirred at RT for 4 hours, 2 ml of 1 M aqueous $NaHSO_4$ solution are added and two phases formed are separated. The organic layer obtained is concentrated and subjected to preparative HPLC (RP-18). N-[5-(2-Cyclo-pentyl-acetyl)-4,5,6,7-tetrahydro-thiazolo[5,4-c]pyridin-2-yl]-3,5-bis-trifluoromethyl-benzene-sulfonamide is obtained.

$^1$H-NMR/CDCl$_3$ (2 rotamers): 12.3 (bs, 1H), 8.28 (s, 2H), 7.92 (s, 1H), 4.44 (s, 1.2 H), 4.32 (s, 0.8H), 3.79 (t, J=5.5 Hz, 0.8H), 3.16 (t, J=5.6 Hz, 1.2H), 2.55 (m, 1.2H), 2.48 (m, 0.8 H), 2.32 (t, J=6.3 Hz, 1.2H), 2.17 (m, 1H), 1.78 (m, 2H), 1.52 (m, 4H), 1.07 (m, 2 H); $^{13}$C-NMR/CDCl$_3$: 172.12, 168.95, 145.48, 132.84, 132.50, 129.85, 127.03, 125.64, 124.40, 121.68, 114.06, 43.27, 42.49, 40.41, 40.18, 39.69, 38.65, 36.90, 33.08, 25.28, 24.44, 23.37.

Preparation of STARTING MATERIALS

S1. 2-Amino-6,7-dihydro-4H-thiazolo[5,4-c]pyridine-5-carboxylic acid tert-butyl ester (compound of formula IV$_A$ wherein Y is tert-butoxycarbonyl)

A mixture of 19.9 g of 1-BOC-piperidin-4-one, 8.4 g of cyanamide, and 6.4 g of sulfur in 100 ml of pyridine is refluxed under inert atmosphere for 100 minutes. From the mixture obtained solvent is evaporated and the evaporation residue obtained is subjected to flash chromatography over silica gel. 2-Amino-6,7-dihydro-4H-thiazolo[5,4-c]pyridin-5-carboxylic acid tert-butyl ester is obtained.

$^1$H-NMR/CDCl$_3$/d$_6$-DMSO: 5.95 (bs, 2 H), 4.39 (s, 2 H), 3.67 (t, J=5.2 Hz, 2 H), 3.08 (bs, 2 H), 1.43 (s, 9 H); $^{13}$C-NMR/CDCl$_3$/d$_6$-DMSO: 166.17, 153.87, 79.19, 28.86, 27.69, 26.01

Analogously to the method as described in Example S1, but using appropriate starting materials, compounds of Examples S2 and S3 are prepared:

S2. 4-Amino-3-thia-5,11-diaza-tricyclo[6.2.1.0*2,6*]undeca-2(6),4-diene-11-carboxylic acid tert-butyl ester $^{13}$C-NMR: 80.24, 53.09, 52.67, 36.70, 36.19, 28.78.

S3. 2-(3,5-Bis-trifluoromethyl-benzenesulfonylamino)-4,5,6,7-tetrahydro-thiazolo[5,4-c]pyridin-5-ium hydrochloride salt (compound of formula V, wherein R$_1$ is 3,5-trifluoromethylbenzene)

50 ml of saturated etheric hydrochloric add are added to a solution of 9.95 g of 2-(3,5-bis-trifluoromethyl-benzenesulfonylamino)-6,7-dihydro-4H-thiazolo[5,4-c]pyridine-5-carboxylic acid tert-butyl ester in 150 ml of $CH_2Cl_2$ and and the mixture obtained is stirred at RT for 4 hours. From the mixture obtained solvent is evaporated and the evaporation residue obtained is treated with diethylether. A solid precipitates, is filtrated off and dried. 2-(3,5-Bis-trifluoromethyl-benzenesulfonylamino)-4,5,6,7-tetrahydro-thiazolo[5,4-c]pyridin-5-ium hydrochloride salt is obtained.

$^1$H-NMR/CDCl$_3$/d$_6$-DMSO: 13.30 (bs, 1H), 9.86 (bs, 2H), 8.43 (s, 2H), 8.29 (s, 1 H), 4.04 (s, 2 H), 3.21 (t, J=5.8 Hz, 2 H), 2.70 (t, J=5.7 Hz, 2 H); $^{13}$C-NMR/CDCl$_3$/d$_6$-DMSO: 168.35, 145.15, 132.17, 131.83, 131.50, 131.17, 130.20, 127.02, 126.66, 126.47, 124.31, 121.59, 118.87, 109.47, 20.30.

Analogously as described in example S3, but using appropriate starting materials, the compounds of examples S4 and S5 are obtained:

S4. 2-(2,3-Dichloro-benzenesulfonylamino)-4,5,6,7-tetrahydro-thiazolo[5,4-c]pyridin-5-ium hydrochloride salt (compound of formula V, wherein R$_1$ is 2,3-dichlorophenyl)

$^{13}$C-NMR: 168,03, 141.31, 134.17, 134.06, 129.33, 129.23, 128.56, 128.33, 108.80, 19.95.

S5. 2-(3,5-Dichloro-benzenesulfonylamino)-4,5,6,7-tetrahydro-thiazolo[5,4-c]pyridin-5-ium hydrochloride salt (compound of formula V, wherein R$_1$ is 3,5-dichlorophenyl)

$^{13}$C-NMR: 168.03, 141.31, 134.17, 134.06, 129.33, 129.23, 128.56, 128.33, 108.80, 19.95.

The invention claimed is:

1. A compound of formula

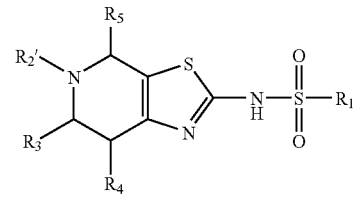

II wherein
R$_1$ is unsubstituted (C$_{6-18}$)aryl, or (C$_{6-18}$)aryl substituted by aminocarbonyl, halogen or halo(C$_{1-6}$)alkyl,
R$_2$' is (C$_{1-12}$)alkoxycarbonyl (C$_{1-6}$)alkylcarbonyl, (C$_{3-6}$)cycloalkyl(C$_{1-6}$)alkylcarbonyl or unsubstituted (C$_{6-18}$) aryl, or (C$_{6-18}$)aryl substituted by aminocarbonyl, halogen or halo(C$_{1-6}$)alkyl,
R$_3$ and R$_5$ together are (C$_{1-4}$)alkylene, and
R$_4$ is hydrogen.

2. A compound of formula

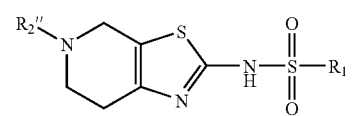

III wherein
R$_1$ is unsubstituted (C$_{6-18}$)aryl, or (C$_{6-18}$)aryl substituted by aminocarbonyl, halogen or halo(C$_{1-6}$)alkyl, and
R$_2$" is (C$_{1-12}$)alkoxycarbonyl, (C$_{3-6}$)cycloalkyl(C$_{1-6}$)alkylcarbonyl, unsubstituted (C$_{6-18}$)aryl, or (C$_{6-18}$)aryl substituted by aminocarbonyl, halogen or halo(C$_{1-6}$)alkyl.

3. A compound according to claim 1, wherein said compound is selected from
N-(3-thia-5, 11-diaza-tricyclo[6.2.1.0*2,6*]undeca-2(6), 4-dien-4-yl-benzenesulfonamide, or a compound of formula III, which is selected from the group consisting of
2-[2-(3,5-Bis-trifluoromethyl-benzenesulfonylamino)-6, 7-dihydro-4H-thiazolo[5,4-c]pyridin-5-yl]-4-trifluoromethyl-benzamide, 2-[2-(2,3-Dichloro-benzenesulfonylamino)-6,7-dihydro-4H-thiazolo[5,4-c]pyridin-5-yl]-4-trifluoromethyl-benzamide, 2-[2-(3,5-Dichloro-benzenesulfonylamino)-6,7-dihydro-4H-thiazolo[5,4-c]pyridin-5-yl]-4-trifluoromethyl-benzamide, 2-(3,5-Bis-trifluoromethyl-benzenesulfonamino)-6,7-dihydro-4H-thiazolo[5,4-c]pyridine-5-carboxylic acid tert-butyl ester, 2-(2,3-Dichloro-benzenesulfonamino)-6,7-dihydro-4H-thiazolo[5,4-c]pyridine-5-carboxylic acid tert-butyl ester, 2-(3,5-Dichloro-benzenesulfonamino)-6,7-dihydro-4H-thiazolo[5,4-c]pyridine-5-carboxylic acid tert-butyl ester, and N-[5-(2-Cyclopentyl-acetyl)-4,5,6,7-tetrahydro-thiazolo[5,4-c]pyridin-2-yl]-3,5-bis-trifluoro-methyl-benzenesulfonamide.

4. A compound according to claim 2 of formula

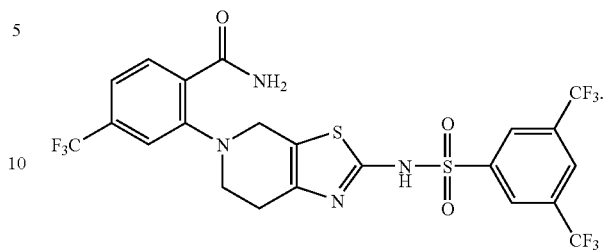

III$_{A1}$

5. A compound of according to claim 1 in the form of a salt.

6. A compound of according to claim 1 for use as a pharmaceutical.

* * * * *